(12) United States Patent
Fugiel et al.

(10) Patent No.: US 8,835,353 B2
(45) Date of Patent: *Sep. 16, 2014

(54) GERMINATION ACCELERATION

(75) Inventors: Judith Fugiel, Lake Villa, IL (US);
Peter D. Petracek, Grayslake, IL (US);
Prem Warrior, Green Oaks, IL (US)

(73) Assignee: Valent BioSciences Corporation,
Libertyville, IL (US)

( * ) Notice: Subject to any disclaimer, the term of this patent is extended or adjusted under 35 U.S.C. 154(b) by 947 days.

This patent is subject to a terminal disclaimer.

(21) Appl. No.: 12/214,560

(22) Filed: Jun. 20, 2008

(65) Prior Publication Data

US 2008/0318782 A1    Dec. 25, 2008

Related U.S. Application Data

(60) Provisional application No. 60/936,498, filed on Jun. 20, 2007.

(51) Int. Cl.
*A01N 43/06* (2006.01)
*A01N 43/12* (2006.01)
*A01N 43/90* (2006.01)

(52) U.S. Cl.
CPC ..................... *A01N 43/90* (2013.01)
USPC ............ 504/100; 504/136; 504/140; 504/296

(58) Field of Classification Search
USPC .................. 504/136, 100, 296, 140
See application file for complete search history.

(56) References Cited

U.S. PATENT DOCUMENTS

| | | | |
|---|---|---|---|
| 4,411,685 A | | 10/1983 | Welebir |
| 4,749,402 A | * | 6/1988 | Garrett et al. ............ 71/28 |
| 5,320,961 A | * | 6/1994 | Zhong et al. ............ 435/424 |
| 2002/0039971 A1 | | 4/2002 | Hayashi et al. |

FOREIGN PATENT DOCUMENTS

| | | |
|---|---|---|
| WO | WO 9844798 A1 * | 10/1998 |
| WO | WO 2005/115142 | 12/2005 |

OTHER PUBLICATIONS

Jonas, O. Improvement of Arable Yields by Treating Seeds with Gibberellic Acids, HU 53753, Feb. 1989, Derwent Abstract, pp. 1-2.*
Palevitch, D., Dormancy-Release of Celery Seed by a Growth Retardant, N-Dimethylaminosuccinamic Acid, 1971, Planta (Berl.), vol. 100, pp. 70-372.*
EP Search Report issued Mar. 13, 2012.
Emongor et al., Effect of promalin on growth and development of kale (*Brassica oleracea* L. Vaqr. Acephala DC), Journal of Agronomy, Asian Network of Scientific Information, vol. 3, No. 3, Jan. 1, 2004 pp. 208-214, XP009156847.
Lee et al., "Effects of fruit drop and polyembryony of *Ardisia pusilla* as influenced by calcite, promalin, and 2,4-DP", Horticulture Environment and Biotechnology, Korean Society for Horticultural Science, Jan. 1, 2006, pp. 93-99, XP009156879.
Shatat et al. "Effect of promaline and gibberellic acid (GA3) on germination of mahaleb cherry seeds", Dirasat: A Learned Research Journal, University of Jordan, The Deanship of Academic Research, Jan. 1, 1985, XP009156881.
Holdsworth et al., "Genetic control mechanisms regulating the initiation of germination", Journal of Plant Physiology, Fischer, Stuttgart, De, Jan. 1, 2001, pp. 439-445, XP004955039.
Auer, "Cytokinin inhibition of arabidopsis root growth: an examination of genotype, cytokinin activity, and N6-benzyladenine metabolism", Oct. 1, 1996, Journal of Plant Growth Regulation, Springer Verlag, pp. 201-206, XP009156872.
Ono et al., "Effects of growth regulators and potassium nitrate on 'Volkameriana' lemon seed germination", Scientia Agricola, 1993, XP002670442.

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

A composition comprising an effective amount of GA4/7 (gibberellin 4 and gibberellin 7) or GA3 (gibberellic acid) and 6BA (benzyladenine) is used as a seed treatment on sweet and field corn (*Zea mays*) to accelerate plant establishment and to promote low temperature germination and emergence.

9 Claims, No Drawings

GERMINATION ACCELERATION

FIELD OF THE INVENTION

The present invention relates to the field of seed treatment. More specifically, the invention relates to the use of a combination of $N^6$-benzyladenine (6BA) and gibberellin 4/7 (GA4/7) or gibberellin 3 (gibberellic acid) to accelerate low temperature germination of corn.

BACKGROUND OF THE INVENTION

In the commercial production of crops, it is desirable to be able to plant seeds early. For example, early planting of seed crops during sub-optimal cold soil temperatures may allow farmers to improve yields by extending the growing season (Lawton, *Progressive Farmer*, April 2007: B-1 to B-3) and help manage busy planting schedule. Also, early planting may permit the planting of warmer growing zone varieties of crops. However, currently, minimum germination temperatures limit crop establishment in early spring and require many seeds to be planted later in the season. Accordingly, a seed treatment that would promote cold temperature germination would be useful.

Seed priming has been used to accelerate cold temperature germination. However, priming requires the seed be exposed to water for a period of time. Also, the process of priming requires a large facility and is not readily useable for large crops.

Therefore, there is a need in the art for an alternative to seed priming. Application of a seed treatment can be logistically simpler and more flexible in allowing a range of chemical treatments that produce different physiological effects, depending on the crop, active ingredient, and rate of application.

SUMMARY OF THE INVENTION

The present invention is generally directed to seed treatment formulations suitable to accelerate crop germination comprising an effective amount of a combination of GA4/7 or GA3 and 6BA. In a preferred embodiment, said crop is corn.

In another embodiment, the present invention is generally directed to a method of accelerating crop plant germination comprising applying to said crop an effective amount of a combination of GA4/7 or GA3 and 6BA.

DETAILED DESCRIPTION OF THE INVENTION

For the purposes of this Application, the definitions are as follows:

6BA ($N^6$-benzyladenine) is defined as $N^6$-phenylmethyl-1H-purin-6-amine;

CPPU (forchlorfenuron) is defined as 1-(2-chloro-4-pyridyl)-3-phenylurea;

GA3 (gibberellic acid) is defined as ($1\alpha,2\beta,4a\alpha,4b\beta,10\beta$)-2,4a,7-trihydroxy-1-methyl-8-methylenegibb-3-ene-1,10-dicarboxylic acid 1,4a-lactone; and GA4/7 (gibberellin 4 and gibberellin 7) is defined as mixture of GA4 (($1\alpha,2\beta,4a\alpha,4b\beta,10\beta$)-2,4a-dihydroxy-1-methyl-8-methylenegibb-1,10-dicarboxylic acid 1,4a-lactone) and GA7 (($1\alpha,2\beta,4a\alpha,4b\beta,10\beta$)-2,4a,7-trihydroxy-1-methyl-8-methylenegibb-1,10-dicarboxylic acid 1,4a-lactone).

In one embodiment, the present invention generally relates to seed treatment formulations suitable to accelerate crop germination comprising an effective amount of a combination of GA4/7 or GA3 and 6BA. In a preferred embodiment, said crop is corn.

In another embodiment, the present invention generally relates to methods of accelerating crop germination comprising applying to crops an effective amount of a combination of GA4/7 or GA3 and 6BA.

The effective amount of a composition comprising an effective amount of a combination of GA4/7 or GA3 and 6BA is such an amount of a combination of GA4/7 or GA3 and 6BA, application of which results in the acceleration of crop germination as compared to crop germination in the absence of the composition. The effective amount can vary depending on the crop and is generally in the range of about 0.5 ppm to about 10,000 ppm of each of GA4/7 or GA3 and 6BA; more preferably from about 1 ppm to about 1,000 ppm of each of GA4/7 or GA3 and 6BA, and most preferably from about 2 ppm to about 100 ppm of GA4/7 or GA3 and 6BA. It is well within a skill of a person of ordinary skill in the art to determine an effective amount of a combination of GA4/7 or GA3 and 6BA for a specific crop.

In one embodiment of the invention, the effective amount of GA4/7 or GA3 is in the range of 0.5 to 200 ppm and the effective amount of 6BA is in the range of 0.3 to 30 ppm.

In another embodiment of the invention, the effective amount of GA4/7 or GA3 is in the range of 2 to 100 ppm and the effective amount of 6BA is in the range of 1 to 10 ppm.

The ratio of GA4/7 or GA3 to 6BA is in the range of from 20:1 to 2:1, preferably from 10:1 to 5:1.

Surprisingly and unexpectedly, Applicants have discovered that applying a composition comprising a combination of GA4/7 or GA3 and 6BA to corn seeds significantly increased the percent of early germination as compared to applying GA3, GA4/7, 6BA, or CPPU alone. Moreover, coleoptile length of seeds treated with a composition comprising a combination of GA4/7 and 6BA was significantly longer than coleoptile length of seeds treated with either GA4/7 or 6BA separately, strongly suggesting a synergistic effect of GA4/7 and 6BA combination.

In an embodiment of the present invention, the seeds are treated with solutions comprising a combination of GA4/7 or GA3 and 6BA. The amount of the solutions is enough to wet the seeds. Techniques of seed treatment application are well known to those skilled in the art, and they may be readily used in the context of the present invention. The compositions of the present invention may be applied as a slurry or soak. Film coating and encapsulation may also be used. The coating processes are well known in the art and employ the techniques of film coating, encapsulation, immersion, etc. The methods of application of the compositions of the present invention may be varied, and the invention is intended to include any technique that is to be used by one of skill in the art.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

Throughout the application, the singular forms "a," "an," and "the" include plural reference unless the context clearly dictates otherwise.

The following examples are intended to illustrate the present invention and to teach one of ordinary skill in the art how to make and use the invention. They are not intended to be limiting in any way.

For all seed treatments, 1 ppm active ingredient refers to 1 microgram active ingredient per gram of seed. For these studies, GA3, GA4/7, 6BA, or CPPU were each dispensed into a 15 ml centrifuge tube, and 2.5 ml of de-ionized water was then added to each tube. The solution was mixed on a vortex mixer and 0.25 ml of this solution was then placed in another 50 ml. centrifuge tube along with 10 grams of sweet corn seed (cv. Silver Queen) or field corn (cv. Hybrid 2652) seed and rotated 360° on a Labquake Rotissarie for 10 minutes to ensure proper seed coverage. To simulate commercial seed treatments, the amount of solutions was just sufficient to wet the seeds. Seeds were dried overnight in weigh boats.

Pouch studies: A CYG germination pouch was drenched with 17 ml of 10° C. de-ionized water. Three treated seeds were placed in the trough of the germination paper, contained within the pouch. Pouches were placed in a Nalgene plastic container cooled to 10° C. The container was incubated in a 10° C. growth chamber with a 16 hour light cycle for the duration of the study. Seedling coleoptiles and radicles were measured by removing the seedling from the pouch and measuring with a ruler.

Petri plate studies: Each standard petri plate (100 mm×50 mm) contained 1 blue Anchor germination circle (3¼ inches in diameter) drenched with 7 ml of de-ionized water cooled to 10° C. Each treatment consisted of 4 petri plates of 10 seeds each. After plating, the petri plates were placed in a Nalgene plastic container cooled to 10° C. This in turn was incubated in a 10° C. growth chamber with a 16 hour light cycle for the duration of the study. Counts were made by visually examining each seed for radicle and coleoptile protrusion.

Pro-Mix studies: Pro Mix potting media was cooled to 10° C. and then placed in a 20 inch×10 inch flat to a depth of 5 cm. A trough of twenty seeds/treatment were planted at a depth of 2 cm. Four trays of twenty seeds each were planted per treatment. The trays were incubated in a growth chamber set at 10° C., 16 hour light cycle. Corn emergence counts were made daily.

EXAMPLES

Example 1

Sweet corn seeds (cv. Silver Queen) were treated with solutions containing 100 ppm GA4/7 or 10 ppm 6BA alone or as a combination of 100 ppm GA4/7 and 10 ppm 6BA in a pouch and held at 10° C. The amount of applied is expressed as ppm or micrograms of compound per gram of seed. GA4/7 at 100 ppm applied with 6BA 10 ppm had greater percents of coleoptile emerged and longer coleoptile length than either treatment alone (Table 1).

TABLE 1

Effect of seed treatments with GA4/7 and 6BA, and combinations of GA4/7 and 6BA on sweet corn (cv. Silver Queen) coleoptile growth in pouches at 10° C. (n = 6 replicate pouches of 3 seeds per pouch).

| Treatments | Coleoptile length (cm) at 22 days after treatment | Coleoptile length (cm) at 22 days after treatment minus the control | Radicle length (cm) at 22 days after treatment |
|---|---|---|---|
| Control | 1.22 | 0 | 2.28 |
| GA4/7 100 ppm | 1.72 | 50 | 3.11 |
| 6BA 10 ppm | 2.17 | 95 | 2.78 |
| GA4/7 100 ppm + 6BA 10 ppm | 3.17 | 195 | 2.83 |

Additionally, preliminary studies showed that high rates of 6BA (>10 ppm) and high rates of GA4/7 (>100 ppm) substantially reduced seedling quality and made seedlings weak and spindly. Seedlings from the combination treatment of 100 ppm GA4/7 and 10 ppm 6BA were not weak and spindly. Furthermore, preliminary studies showed that high rates of 6BA (>10 ppm) reduced radicle growth. Table 1 shows that compared to the control, radicle growth was increased most by GA4/7 (100 ppm), but radicle growth was also increased by treatments of 10 ppm 6BA and the combination of 100 ppm GA4/7 and 10 ppm 6BA. Taken together, these results demonstrate that combinations of these lower rates of GA4/7 and 6BA can be used to accelerate low temperature germination and growth without substantially weakening the seedling.

Example 2

Sweet corn (cv. Silver Queen) seeds were treated with solutions containing GA4/7, 6BA, or GA4/7 and 6BA, planted into ProMix soil, and held at 10° C. At 22 days after treatment, more seedlings from seeds treated with the combination treatment of GA4/7 and 6BA had emerged than seeds treated with 6BA or GA4/7 alone (Table 2). The length of the emerged coleoptiles at 32 days after treatment was significantly longer for the GA4/7 and 6BA combination treatment than GA4/7 and the 6BA treatment had no significant effect compared to the control. This demonstrates that GA4/7 and 6BA worked synergistically to increase the growth of the corn coleoptile.

TABLE 2

Effect of seed treatments with 6BA and GA4/7 alone and in combination on emergence and coleoptile length of sweet corn (cv. Silver Queen) in ProMix at 10° C. (n = 4 replicates of 20 seeds).

| Treatments | Percent coleoptile emergence at 22 days after treatment | Coleoptile length above ground (mm) at 32 days after treatment |
|---|---|---|
| Control | 3.7 | 13.9 |
| 6BA 10 ppm | 6.2 | 17.1 |
| GA4/7 100 ppm | 8.7 | 31.2 |
| 6BA 10 ppm + GA4/7 100 ppm | 17.5 | 47.1 |

Example 3

Sweet corn (cv. Silver Queen) seeds were treated with solutions containing GA3, 6BA, or GA3 and 6BA, planted into ProMix soil, and held at 10° C. At 21 days after treatment, 6BA (10 ppm) or GA3 (100 ppm) alone did not increase percent coleoptile emergence (Table 3). However, the combination treatment of GA3 and 6BA greatly increased the percent emergence. This demonstrates that GA3 and 6BA worked synergistically to increase the growth of the corn coleoptile.

TABLE 3

Effect of seed treatments with 6BA and GA3 alone and in combination on emergence and coleoptile length of sweet corn (cv. Silver Queen) in ProMix at 10° C. (n = 4 replicates of 20 seeds).

| Treatments | Percent coleoptile emergence at 21 days after treatment |
| --- | --- |
| Control | 5.0 |
| 6BA 10 ppm | 3.7 |
| GA3 100 ppm | 1.2 |
| 6BA 10 ppm + GA3 100 ppm | 11.2 |

Example 4

Sweet corn seeds (cv. Silver Queen) were treated with solutions containing GA4/7 or CPPU or combinations of GA4/7 and 6BA or GA4/7 and CPPU, plated onto wetted paper in a petri plate, and held at 10° C. Percent coleoptile emergences of seeds treated with GA4/7 and 6BA were significantly greater than GA4/7 alone (Table 4). In contrast, CPPU did not increase emergence alone or in combination with GA4/7. This suggests that the synergistic activity of 6BA with GA4/7 is not general for all cytokinins.

TABLE 4

Effect of seed treatments with GA4/7 alone or in combination with CPPU or 6BA on emergence and coleoptile length of sweet corn (cv. Silver Queen) in petri plates at 10° C. (n = 5 replicates of 10 seeds).

| Treatments | Percent coleoptile emergence at 14 days after treatment |
| --- | --- |
| Control | 2 |
| GA4/7 10 ppm | 24 |
| GA4/7 100 ppm | 32 |
| CPPU 1 ppm | 0 |
| CPPU 10 ppm | 4 |
| CPPU 1 ppm + GA4/7 10 ppm | 30 |
| CPPU 10 ppm + GA4/7 10 ppm | 28 |
| CPPU 1 ppm + GA4/7 100 ppm | 28 |
| CPPU 10 ppm + GA4/7 100 ppm | 34 |
| 6BA 10 ppm + GA4/7 100 ppm | 58 |

Example 5

Hybrid field corn seeds (cv. Hybrid 2652) were treated with solutions containing GA4/7 or 6BA or combinations of GA4/7 and 6BA, plated onto wetted paper in a petri plate, and held at 10° C. GA4/7 at 10 ppm did not significantly increase coleoptile emergence compared to the control (Table 5). However, treatment with GA4/7 and 6BA significantly increased germination compared to treatment with GA4/7 or 6BA alone. This suggests combining GA4/7 and 6BA synergistically increased the low temperature germination of Hybrid field corn seeds.

TABLE 5

Effect of seed treatments with GA4/7 alone or in combination with 6BA on coleoptile emergence of hybrid field corn (Hybrid 2652) on petri plates at 10° C. (n = 5 replicates of 10 seeds).

| Treatments | Percent coleoptile emergence at 12 days after treatment |
| --- | --- |
| Control | 5 |
| GA4/7 10 ppm | 15 |
| 6BA 10 ppm | 32 |
| GA4/7 10 ppm + 6BA 4/7 10 ppm | 70 |

The invention claimed is:

1. A method for accelerating *Zea mays* germination comprising applying to seed of said *Zea mays* an effective amount of gibberellin 4/7 or gibberellic acid and an effective amount of benzyladenine, wherein the effective amount of gibberellin 4/7 or gibberellic acid is from 2 ppm to 100 ppm and the effective amount of benzyladenine is from 2 ppm to 100 ppm and wherein the ratio of gibberellin 4/7 or gibberellic acid: benzyladenine is 10:1 to 5:1.

2. The method of claim 1, wherein said *Zea mays* is sweet corn.

3. The method of claim 1, wherein said *Zea mays* germinates at temperatures as low as 10 degrees Celsius.

4. The method of claim 1, wherein the effective amount of gibberellin 4/7 is from 2 ppm to 100 ppm and the effective amount of benzyladenine is from 2 ppm to 10 ppm.

5. The method of claim 1, wherein the effective amount of gibberellic acid is from 2 ppm to 100 ppm and the effective amount of benzyladenine is from 2 ppm to 10 ppm.

6. A method for increasing the yield of *Zea mays* comprising applying to seed of said *Zea mays* an effective amount of gibberellin 4/7 or gibberellic acid and an effective amount of benzyladenine, wherein the effective amount of gibberellin 4/7 or gibberellic acid is from 2 ppm to 100 ppm and the effective amount of benzyladenine is from 2 ppm to 100 ppm; and wherein the ratio of gibberellin 4/7 or gibberellic acid: benzyladenine is 10:1 to 5:1.

7. The method of claim 6, wherein said *Zea mays* is sweet corn.

8. The method of claim 6, wherein the effective amount of gibberellin 4/7 is from 2 ppm to 100 ppm and the effective amount of benzyladenine is from 2 ppm to 10 ppm.

9. The method of claim 6, wherein the effective amount of gibberellic acid is from 2 ppm to 100 ppm and the effective amount of benzyladenine is from 2 ppm to 10 ppm.

* * * * *